United States Patent
Tjerneld et al.

(10) Patent No.: US 6,454,950 B1
(45) Date of Patent: Sep. 24, 2002

(54) SEPARATION METHOD UTILIZING LIQUID-LIQUID PARTITION

(75) Inventors: Folke Tjerneld, Malmö (SE); Josefine Persson, South San Francisco, CA (US); Hans Olof Johansson, Mölndal (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/869,657

(22) PCT Filed: Dec. 30, 1998

(86) PCT No.: PCT/SE98/02469

§ 371 (c)(1),
(2), (4) Date: Oct. 3, 2001

(87) PCT Pub. No.: WO00/40598

PCT Pub. Date: Jul. 13, 2000

(51) Int. Cl.[7] ............................................... B01D 11/04
(52) U.S. Cl. .................. 210/734; 210/638; 210/639; 210/774; 210/805; 210/806; 530/422; 530/427
(58) Field of Search ............................... 210/632, 634, 210/635, 638, 639, 774, 805, 806, 742, 743; 530/412, 413, 415, 422, 427

(56) References Cited

U.S. PATENT DOCUMENTS 5,078,886 A * 1/1992 Hsu ........................... 210/634
5,772,888 A * 6/1998 Liu et al. .................... 210/634
6,048,715 A * 4/2000 Haynes et al. .............. 530/413

FOREIGN PATENT DOCUMENTS

WO  WO 98 11127  3/1998

OTHER PUBLICATIONS

Hirofumi Tani, et al. "Aqueous Micellar Two-Phase Systems for Protein Separation" Analytical Sciences, vol. 14, Oct. 1998, pp. 875–888.

* cited by examiner

Primary Examiner—Joseph W. Drodge
(74) Attorney, Agent, or Firm—Royal N. Ronning, Jr.; Stephen G. Ryan (57) ABSTRACT

A method for the separation of a predetermined compound comprising i) partitioning the compound in a two-phase (system A) in which at least one of the phases is rich (phase 1) and the other is poor (phase 2) in a thermoseparating polymer (I), ii) collecting one phase (phase 1 or phase 2) containing said compound, and iii if desired, further working up said compound from the phase collected in step ii, characterized a) in that polymer (I) is a micell-forming thermoseparating polymer, and b) in that phase 2 possibly contains at least one agent that is cloud point-decreasing for thermoseparating polymer (I), such as a polymer (II) that is incompatible with polymer (I) or a salt.

22 Claims, 3 Drawing Sheets

SEPARATION METHOD UTILIZING LIQUID-LIQUID PARTITION

This application is a 371 of PCT/SE98/02469, filed on Dec. 30. 1998.

TECHNICAL FIELD

The present invention concerns separations in aqueous phase systems containing at least one aqueous phase containing a thermoseparating polymer. The compounds to be separated may be of biological nature (biomolecule) having for instance lipid, peptide and/or carbohydrate structure.

TECHNICAL BACKGROUND

The traditional aqueous two-phase systems have been the PEG/dextran and PEG/salt systems (PEG=poly(ethylene glycol). The former system derives from polymer-polymer incompatibility and the latter from salting out of the polymer with a salt. The PEG/dextran systems are used for small scale separations of macromolecules, membranes, cell particles and cells (Albertsson, Partitian of cell particles and macromolecules, $3^{rd}$ ed., Wiley, New York; and Walter et al. (Ed.), Aqueous two-phase systems, meth. Enzym. 228 (1994 (Academic Press, London)). The PEG/salt systems are mainly used in large scale enzyme extractions (Cordes et al., Meth. Enzymol. 228 (1994) 640–608 (Academic Press, London).

More novel two-phase systems have utilized polymers that have a solubility in water that decreases upon increasing the temperature (thermoseparating polymers). In these cases two macroscopic phases (one polymer enriched bottom phase and one water rich top phase) can be obtained upon heating a solution of the polymer a few degrees above the cloud point, i.e. the temperature at which the phases start to separate out. The cloud point for an aqueous solution of a given polymer depends on polymer concentration and amount and type of other components added (for instance cloud point-decreasing agents). The lowest cloud point is called the lowest critical solution temperature (LCST) (Saeki et al., Polymer 17 (1976) 685–688). This phenomenon also occurs in water solution of non-ionic surfactants e.g. Triton X-114, C12E05. Applications of thermoseparations in biotechnology have been reviewed (Galaev et al, Enzyme Microb. Technol. 15(1993) 354–366). If not otherwise specified, LCST will refer to the lowest cloud point for a system consisting of a pure polymer and pure water.

Many thermoseparating polymers contain ethylene oxide groups. PEG as such is one example but its cloud point is too high (above 100° C.) for use in a thermoseparating process for the separation of biomaterials Ethylene oxide (EO)-propylene oxide (PO) random copolymers have lower cloud points. Ucon 50 HB-5100 and Breox 50A 1000 are random copolymers composed of 50% EO and 50% PO groups (EOPO-polymers). Both copolymers have a LCST at 50° C.

Phase systems of polymers having various EO/PO ratios have been studied in the separation of proteins (Harris et al., Biosep. 2 (1991) 237–246; Alred et al., J. Chromatogr. 659 (1994) 289–298; Persson et al., Chromatogr. 711 (1998) 97–109; Berggren et al., J. Chromatogr. A 718 (1995) 67–79; Johanssson et al., Biochim. Biophys. Acta 1290 (1996) 289–298). Thermoseparating polymers consisting of blocks of EO and PO units (Pluronics) and their use for separation of an enzyme have been described (Tani et al., Analytical Science 13 (1997) 925–929). The polymers used by Tani et al have a hydrophilic EO block in the middle and less hydrophilic PO blocks as terminal groups or vice versa (EOPO block copolymer).

Two of the inventors (Folke Tjerneld and Josefine Persson) are also an inventor in WO 9811127 and WO 981140 both of which describe purification of apolipoprotein in aqueous two phase systems containing a thermoseparating polymer.

Partition of amino acids and oligopeptides having various hydrophobicity and net charge has been studied in the water/Ucon system (Johansson et al., Biosep. 5 (1995) 269–279; (Johansson et al., Biochim. Biphys Acta 1335 (1996) 315–325).

Disadvantages with thermoseparating polymers used so far and objectives with the invention.

In phase systems containing thermoseparating polymers the polymer phase so far always has contained relatively large concentrations of polymer (above 40%) with most proteins exclusively distributing to the water phase. It would be beneficial a) to have systems in which there are less polymer in the polymer phase, b) to be able to direct the compound to be separated back and forth between the phases and c) to have separation processes in which recirculation of the thermoseparating polymer is facilitated.

DEFINITIONS

Polymers:

When the term polymer is used in the present invention it refers to water-soluble/water-miscible polymers if not otherwise emphasised. By a polymer is further meant that it contains $\geq 20$ monomeric units that may be different or equal.

Thermoseparating polymers are polymers having water-solubilities that decrease upon increasing the temperature.

Cloud point-decreasing agents are compounds that when added to a polymer-water solution decrease the cloud point of the solution.

Cloud point-increasing agents are compounds that, when added to a solution of a thermoseparating polymer in water increase the cloud point of the solution.

Incompatible polymers. In the context of the present invention a polymer is incompatible with another polymer if two aqueous phases can be formed when both polymers are mixed with water. The definition also encompasses that the first polymer occurs predominantly in one phase and the second polymer predominantly in the other phase.

Micell-forming and non-micell-forming polymers:

Micell-forming properties of a thermoseparating polymer are reflected in cloud point variation when the polymer concentration is varied in a solution consisting of pure water and the polymer. See FIG. 1 where the slightly concave curvature of Breox PAG 50A 1000 (International Speciality Chemicals Lt, Southampton, U.K.) and the strong concave curvature of the hydrophobically modified ethylene oxide propylene oxide random copolymer (HM-EOPO polymer) used in the experimental part reflect that Breox is non-micell forming and the HM-EOPO polymer micell-forming. For the sake of simplicity and in the context of the preferred modes of the invention, a micell-forming thermoseparating polymer is a polymer that, when mixed with water to the concentration of its LCST and raising the temperature from below to above this temperature, will be able to give two phases, both of which have a water concentration of at least 70% such as 80%. Many of these polymers exhibit a pronounced minimum at their LCST. Compare the curves for HM-EOPO polymer (micell-forming) with Breox (non-micell-forming) in FIG. 1. A non micell-forming polymer is a water-soluble/water-miscible polymer that does not comply with the definition of a micell-forming polymer. The percentage values above and below are based on w/w if not otherwise specified.

A non-micell-forming polymer is normally incompatible with a micell-forming polymer meaning that a non-micell-forming polymer often will act as cloud point-decreasing agents in mixtures of water and micell-forming polymers and vice versa for micell-forming polymers when introduced into mixtures of water and non-micell forming polymers.

SUMMARY OF THE INVENTION

It has now been discovered that the objectives discussed above will be met in case one selects a thermoseparating polymer that is micell-forming as defined above. Accordingly the present invention concerns a method for the separation of a predetermined compound comprising i) partitioning the compound in a two-phase system (system A) in which at least one of the phases (phase 1) and the other is poor (phase 2) in a thermoseparating polymer (I), ii) collecting one phase (phase 1 or phase 2) containing said compound, and iii) if desired, further working up said compound from the phase collected in step ii.

The characteristic feature of the method is that a) polymer (I) is a micell-forming thermoseparating polymer, that when mixed with water to the concentration of its lowest critical solution temperature (LCST and raising the temperature from below to above this temperature is capable to give two phases, both of which have a water concentration of at least 70%, and b) phase 2 possibly contains at least one agent that is cloud point-decreasing for the thermoseparating polymer (I), such as a polymer (II) that is incompatible with polymer (I) or a salt.

Polymer (II) will in the normal case predominantly be present in phase 2.

The two-phase system may be part of a multi-phase system that contains additional aqueous liquid phases containing one or more additional water-soluble polymer.

By the expression that one phase is rich in and the other phase poor in a polymer does only refer to that one phase contains more than the other of the polymer (often more than times).

The two phases may be obtained by premixing the necessary components including the sample containing the compound to be separated at a temperature below the cloud point of the system and them increasing the temperature to become above the cloud point of the system. An alternative is to mix the components of a given two-phase system at a temperature that is above the cloud point of the final system.
Recirculation of polymers.

The polymers of the phases may be recirculated and used as polymer (I) and polymer (II), respectively, in step (i) in a second run of the process. This can be done by recirculation of the phases directly in case they contain no significant amounts of the compound to be separated and/or other undesired components. Otherwise it is preferred to carry out further separation steps, for instance:

Polymer (I): Phase 1 is subjected to a second phase separation step, for instance by adding water and/or one or more cloud point-decreasing agent and/or by raising the temperature above the cloud point of the phase system formed and based on phase 1. This phase separation step results in phase 1:1 (rich in polymer (I)) and phase 1:2 (poor in polymer (I)). If necessary buffering substances and substances that are able to direct partition of the component to be separated in step (i) and/or of undesired components to phase 1:2 are added. If so desired phase 1:1 can then be recirculated possibly after further enrichment with respect to polymer (I).

Polymer (II): If polymer II is a thermoseparating polymer the same principles as for phase 1 can be applied for recirculation of phase 2. For instance water and/or a cloud point decreasing agent can be added, possibly followed by a increase in temperature in order to achieve separation of phase 2 into one phase rich and one phase poor in polymer (II) (phase 2:1 and phase 2:2, respectively). If so desired, phase 2:1 can then be recirculated back and used as polymer (II) in step (i) of a second run of the process.

In case polymer (I) and/or polymer (II) is/are recirculated it may be necessary to supplement with further amounts of respective polymer to system A in step (i) of a second run.
Thermoseparating polymer (I) (micell-forming polymer)

The total amount of polymer (I) in system A normally is at most 50%. One of the most important advantages with the invention is that our selection of polymer (I) enables polymer concentrations below 20% and even below 10% (w/w).

Useful micell-forming thermoseparating polymers typically will have a LCST that is $\leq 90°$ C.; often with preference for those having LCST $\leq 50°$ C., such as $\leq 40°$ C. or $\leq 20°$ C. Proteins and other compounds having oligo- or polypeptide structure often are temperature sensitive and therefore will require polymers with LCST $\leq 40°$ C. or $\leq 20°$ C. Compounds with lipid or carbohydrate structure on the other hand are often more temperature stable, enabling the use of micell-forming thermoseparating polymers having LCST up to 90° C. or higher. A polymer with a lower LCST will be preferred to a polymer with a higher LCST for practical reasons (less need for heating).

Figure 1:
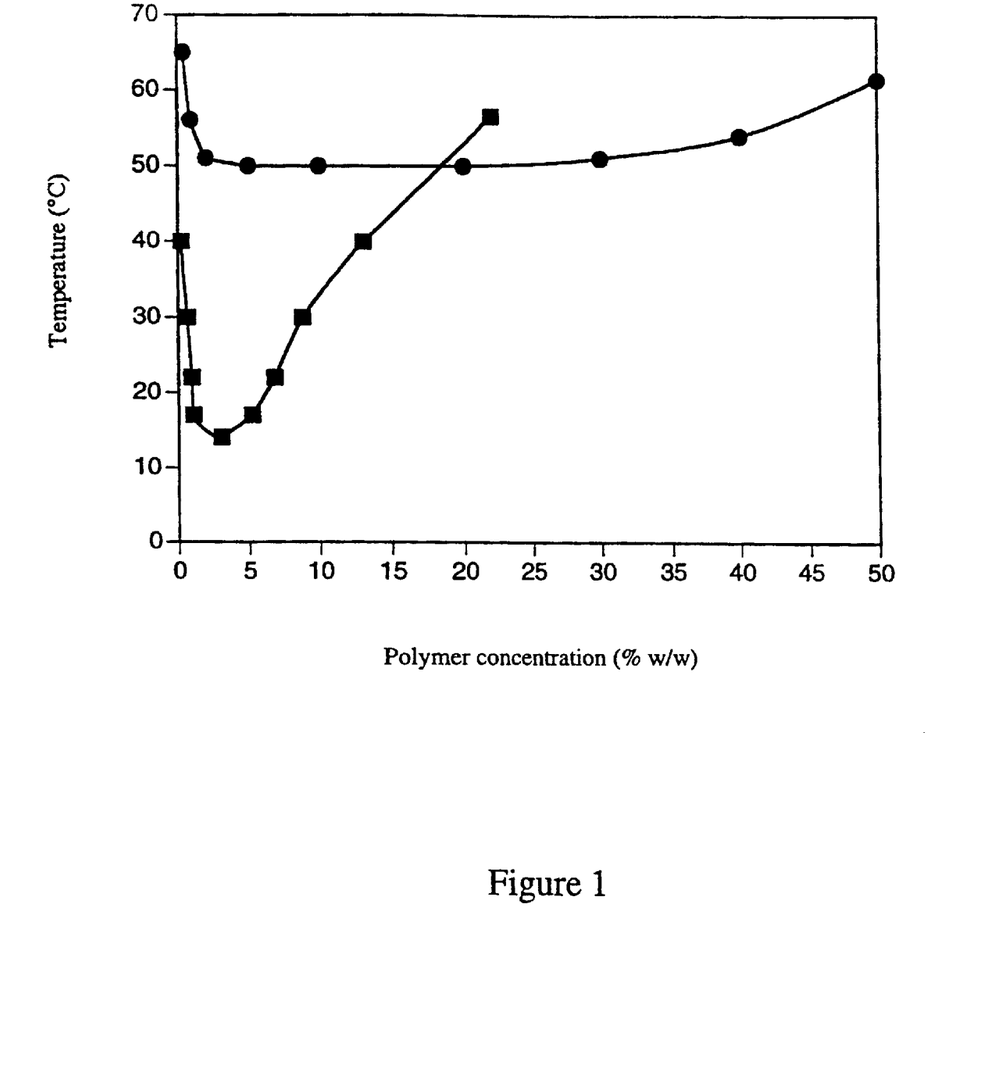
FIG. 1 shows the effect of different temperatures on the polymer concentrations in a two phase separation.

Selection of suitable polymers can be achieved by testing, for instance by mixing a thermoseparating polymer having a cloud point as defined above with pure water and determining the cloud point at different polymer concentrations and constructing phase diagrams as given in FIG. 1 and described in corresponding experimental part.

The initial selection of polymers to be tested may be among water-soluble thermoseparating polymers that contain a plurality of structures present in known thermoseparating polymers, for instance those given by Galaev et al (Enzyme Microbiol. Technol. 15 (1993) 354–366).

It is believed that the key feature of a micell-forming polymer suitable for the invention is a central polymeric part built up of identical or different hydrophilic monomeric units and terminal ends that consist of a respective hydrophobic group. The hydrophilic monomeric units (containing only carbon, hydrogen and oxygen atoms) should exhibit a ratio between number of oxygen atoms and number of carbon atoms that is at least 1/4, with preference for at least 1/3. The hydrophobic terminal groups (containing only oxygen, carbon and hydrogen atoms) should exhibit a ratio between number of oxygen atoms and number of carbon atoms that is at most 1/5. For other types of hydrophilic and hydrophobic groups similar rules apply for hydrophilicity and hydrophobicity, respectively.

The central part of the polymer may be a straight or branched chain. The central part may consist of a number of different or identical subunits, each of which is built up of a straight chain of hydrophilic monomeric units as defined above and each subunits being linked to another subunit by a divalent bridge not being part of the subunit and not imparting water-insolubility to the polymer in total. The bridges may comprise one or more structural elements selected from straight, branched or cyclic divalent $C_{2-6}$- hydrocarbon group, —CH=CH—, —C≡C—, —N=N—, —O—, —S—, —SO$_2$—, —CONR$^1$—, —COO—, —NR$^2$R$^3$—, —SO$_2$NR$^1$—, —OCO—, —NR$^1$CONR$^2$—, —NR$^2$COO— where R$^{1-3}$ are selected among hydrogen and lower hydrocarbon groups containing 1–12 carbon atoms, such as C$_{1-12}$-alkyls -arylalkyls and -alkylaryls.

In preferred variants the monomeric units are selected among ethylene oxide and straight or branched propylene oxide, e.g. as a random or block copolymerisate or as a homopolymerisate, either as the central part or as a subunit of polymer (I) (random or block EOPO polymers, respectively).

The hydrophobic groups may be identical or different. They may be selected among hydrocarbon groups containing 10–30 sp$^3$-hybridised carbon atoms in which, for instance, 1–4 of the carbon atoms possibly are replaced with any of the structural elements given above for bridges linking subunits together.

The synthesis of suitable polymers has been described in EP 260430.

Cloud point-decreasing agent for aqueous solutions of polymers.

This agent may be a salt which is soluble in one or both of the phases (water-soluble) or a second polymer (II) that is non-micell-forming and/or non-compatible with polymer (I), and therefore mainly will be present in phase 2. Also low-molecular weight water-soluble non-ionic compounds may act as cloud point decreasers.

Suitable salts may be selected among water-soluble sodium, potassium and ammonium (R$^4$R$^4$R$^6$R$^7$N$^+$ where R$^{4-7}$ may, for instance, be selected from hydrogen and C$_{1-30}$ alkyls, aryls, aralkyls and alkaryls) salts of chloride, bromide, acetate, phosphate (PO$_4^{3-}$; HPO$_4^{2-}$; H$_2$PO$_4$) sulphate (SO$_4^{2-}$) etc.

Polymer (II) may be selected among polymers that are incompatible with polymer (I), for instance by having a low tendency to form micelles. Examples are polysaccharides, such as cellulose, dextran, starch etc., which, if necessary, may have been appropriately derivatized and/or fragmented, random or block copolymers between ethylene oxide and propylene oxide without derivatised terminals, polyethylene glycol. Polymer (II) may be a thermoseparating polymer that is incompatible with polymer (I), for instance selected among those given by Galaev et al (Enzyme Microb. Technol. 15(1993) 354–66). See also under the discussion above about the polymers sold under the trade names Breox, Ucon and Pluronics.

Cloud point-decreasing agents for aqueous solutions of thermoseparating forms of polymer (II) may be selected along the same lines as for polymer (I) with the exception that the polymer variants should be incompatible with polymer (II).

Cloud point-increasing agents.

Examples are aliphatic alcohols, charged detergents etc. This type of agents are normally not added in order to increase the cloud point of a system, but for utilizing some other properties that they have. For instance charged detergents can be used for favouring partition of the compound to be separated to a particular phase Means for directing the compounds to be separated between different phases.

The partition of a compound may depend on the electrical charge of a compound. In case the charge is pH-dependent, pH of the phase system may be adjusted to achieve maximal partition of the compound to the phase to be collected in step (ii) of the inventive method. Illustrative examples of compounds that may have a pH-dependent charge are compounds exhibiting oligo- or polypeptide structure.

The partition coefficient depends on temperature. Therefore the temperature may be varied to achieve maximal partition of the compound to the phase collected in step (ii) of the method.

A third alternative to accomplish maximal partition to the phase to be collected in step iii) is to incorporate in the phase system a substance that have the ability to associate with and thereby stabilize the compound to be separated in the phase to be collected in step ii (improved partition). Illustrative examples are detergents and salts.

Maximal partition includes that pH, temperature and/or the substance that associates with the compound to be separated are adapted so that an optimal or a maximal amount of the compound is partitioned to the desired phase. For associating substances this include type as well as amount.

In case the compound to be separated is electrically charged its partition will depend on the type of counterions that are present. The addition of a soluble salt will often change the counterion profile of the system and may therefore also change the partition of the compound to be separated.

In case the compound to be separated is positively charged then salts containing anions that are relatively large (low concentration of charge) will be able to improve the partition to the more hydrophobic phase, in this case phase 1 (rich in polymer (I)). Typical examples are salts containing halide ions (Cl$^-$, Br$^-$, I$^-$ etc), SCN$^-$, ClO$_4^-$ and anionic surfactants, for instance comprising a carboxylate anion group, a sulphonate anion group (e.g. dodecylsulphonate), a sulphate anion group, a phosphonate anion group, a phosphate anion group.

In case the compound to be separated is negatively charged, then salts containing cations that are relatively large (low concentration of charge) will be able to improve the partition to the more hydrophobic phase. Typical examples are alkyl ammonium salts containing a cation of the general formula R$^4$R$^5$R$^6$R$^7$N$^-$ where R$^{4-7}$ may, for instance, be selected from hydrogen and C$_{1-30}$ alkyls, aryls, aralkyls and alkylaryls. The ammonium moiety may be a primary, secondary, tertiary or quaternary ammonium ion, e.g. cetyltriethyl ammonium, dodecyltriethyl ammonium, triethylammonium and other cationic detergents.

In case one wants to improve the partition of a charged compound to the phase having the lowest concentration of thermoseparating polymer (I) (=phase 2), one should select a water-soluble salt in which the potential counterion to the compound to be separated is small and have a high concentration of charge. Typical salts to be used in for separating positively charged compounds in this case contain anions, such as PO$_4^{3-}$, HPO$_4^{2-}$; H$_2$PO$_4^{2-}$, SO$_4^{2-}$, AcO$^-$ and negatively charged hydrophilic polymers, for instance dextran, starch and the like carrying anionic groups such as carboxylate groups, sulphonate groups, sulphate groups, phosphonate groups, phosphate groups. Typical salts to be used in this case for separating negatively charged compounds are salts in which the cation is a hydrophilic polymer exhibiting primary, secondary, tertiary and/or quaternary ammonium groups (—$^+$NR$^1$R$^2$R$^3$R$^4$ where R$^{1-4}$ are selected among H and C$_{1-12}$ alkyl group, preferably H or one C$_{1-12}$ alkyl group).

Also other types of compounds can be added for improving the partition to a desired phase. A typical example is an affinity counterpart to the compound to be separated, which counterpart has been derivatized to have an improved partition to the desired phase, for instance by being covalently linked to a polymer or any other component having preference for the phase, such as a detergent.

The phase to be collected in step (ii) and further work up.

This phase may be either phase 1 or phase 2 depending on how the components added have been selected and the result this has had on the partition of the compound to be separated. Under certain circumstances both phase 1 and phase 2 are collected and further processed, for instance when the crude starting sample contains two desired compounds that have preference for different phases.

In case the goal is to end up with the compound separated in step (i) in a purified form, it is often of advantage to select the components of the phase system so that the compound ends up in a phase that is poor in polymer (either polymer (I) or polymer (II)), i.e. a water phase. This means that the compound should be directed to phase 2 and in case this is rich in polymer (II) to phase 2:2 or to phase 1:2. To accomplish this, the same principles as outlined above can be applied with or without recirculation of polymer (I) and/or polymer (II).

The compound separated to the phase collected in step (i) may be further worked up, for instance by further two phase separations (e.g. as outlined above), by electrophoresis, liquid chromatography (ion exchange, bioaffinity etc chromatography), precipitation, density gradient centrifugation, extraction, etc.

DETAILED DESCRIPTION OF A BEST MODE OF THE INVENTION

The invention will now be illustrated by the experimental part in which the best mode contemplated at the priority date is given.

EXPERIMENTAL PART
MATERIALS AND METHODS
Materials:

The HM-EOPO polymer used is a random copolymer of ethylene oxide and propylene oxide chains which flank a central group deriving from reacting one end group of each chain with a respective isocyanate group of isophorone diisocyanate. At both of the remaining ends there is a $C_{14}H_{29}$ alkyl group. For the synthesis see EP 260430. The molecular mass of the polymer used was about 7500–8000 Da. The HM-EOPO polymer was obtained from Akzo Nobel, Stenungsund, Sweden. Fatty acid free bovine serum albumin (BSA) was obtained from Boehringer Mannheim, Mannheim, Germany and hen egg lysozyme was obtained from Sigma Chemicals Co, St Louis, Mo., U.S.A. Purified apolipoprotein A-1 was a gift from Pharmacia & Upjohn, Stockholm, Sweden, and was a recombinant variant, Milano, which is a dimeric form in contrast to the normal monomeric form (Persson et al., J. Chromatog. 711 (1998) 97–109). All salts were analytical grade. Millipore water was used in all solutions. A stock solution of triethylammonium phosphate was prepared by titrating triethylammonium with phosphoric acid. Triethyl ammonium phosphate salt solution salt is abbreviated to $Et_3NH$-phosphate. The human plasma and. the *E. coli* extract were gifts from Pharmacia & Upjohn, Stockholm; Sweden. The human plasma contained the normal monomeric form of apolipoprotein A-1.

Phase diagram

Temperature versus polymer concentration phase diagrams were made by separating systems at different temperatures and determining the polymer concentration in the tap and bottom phase, respectively. The polymer concentration was determined by measurements of the refractive index. The refractometer was from Carl Zeiss, Oberkochen/Württ., Germany. The refractive index measurements were performed at 4° C.

The cloud point of the systems were determined by heating a one phase system with magnetic stirring in a water bath. The cloud point was taken as the temperature at which the solution became turbid. The heating rate was less than 1° C/minute.

Salt partitioning studios

The partitioning of salts was measured with conductometry in protein free systems. The polymer concentration was 4% (w/w) and the salt concentration in the system was 50 mM. The phase system containing Na-phosphate was separated at 22° C. and the systems with $Et_3NH$-phosphate and $NaClO_4$, were separated at 27° C. Na-phosphate and $Et_3NH$-phosphate at pH 7 contain the anions $H_2PO_4^-$ and $HPO_4^{2-}$. The samples were allowed to stand and separate overnight in water bath. The conductometer used was a Metrohm 644 (Herisan, Switzerland). Duplicates of all systems were prepared and mean values are given.

Protein partitioning studies

In all experiments with partitioning of pure BSA, lysozyme and apolipoprotein A-1 the salt concentration was 50 mM and the buffer concentration was 10 mM (sodium phosphate pH 7.0). When sodium phosphate was used as salt in the system the total phosphate concentration was 60 mM (i.e. 50 mM salt+10 mM buffer). The polymer concentration was 4% (w/w) and the protein concentration was 1 mg/ml. An 8 g system was prepared and carefully mixed at 0–4° C. At these temperatures all systems were one phase. From each of the cold systems 7 g was removed and put into graduated pipettes, which were sealed at the top and bottom with parafilm. The pipettes, with the systems, were immersed into a water bath at the required solution temperature. The system was first equilibrated at the investigated temperature, remixed and left to separate. The systems were left standing for 2–3 h. The top and bottom phase volumes were read. The phases were carefully separated and analysed. Duplicates of all systems were prepared.

Purification of apolipoprotein from human plasma.

The thermoseparating polymer was added as pure component to the plasma. The total mass of the system was 6.0 g and contained 4% (w/w) HM-EOPO polymer and 3 g human plasma. In some systems 100 mM $NaClO_4$ was added. The total protein concentration in the systems was 15 mg/ml. The pH in the system was 7.8, measured in the mixed system at 22° C. The systems were separated at 26° C. for 80 min in a water bath.

Purification of apolipoprotein from *E. coli* extract.

Recombinant apolipoprotein A-1, variant Milano, was expressed in *E. coli* fermentations. Apolipoprotein A-1 was exported to the periplasmic space and was subsequently obtained in the fermentation broth. The cells were removed by flocculation followed by centrifugation. The supernatant containing apolipoprotein A-1 was concentrated 8 times by ultrafiltration using a membrane with a 10 000 cut off (Persson et al., J. Chromatog. 711 (1998) 97–209). The concentration of apolipoprotein A-1 after ultrafiltration was 2.5 mg/ml (determined with ELISA assay) and the total protein concentration was 27 mg/ml (determined according to Bradford (Anal. Biochem. 72 (1976) 248–254). The buffer in this E. coli extract was 20 mM Tris-HCl pH 8.0, 150 mM NaCl, 10 mM EDTA and 0.1% Tween 80. The purification in the HM-EOPO polymer water system was performed in a 7.0 g system. HM-EOPO polymer concentration was 4% (w/w), E. coli extract, 1.0 g, was added plus 3.7 g of the above buffer. The total protein concentration in the system was 4 mg/ml and apolipoprotein A-1 concentration 0.4 mg/ml. The pH in the system was 7.5 determined in mixed system.

Protein and enzyme determination

Determination of the pure proteins in the phase systems was carried out by mixing 1 g sample with 1 ml 50% (v/v) methanol which prevents thermoseparation in the sample. The protein concentration of this mixture was then determined by UV absorbance at 280 nm. Lysozyme was determined by activity measurements according to Shugar (Shugar, Biochem. Biophys Acta 8 (1952) 302-). The spectrophotometer used was a UV-2101 PC (Shimadzu Co, Kyoto, Japan). The partition coefficient is defined as $K=C^t/C^b$, where $C^t$ and $C^b$ are protein concentrations in the top and bottom phases, respectively. The pH of the system was measured in the top phase removed after the separation.

When purifying apolipoprotein A-1 from human plasma the partitioning of proteins was quantitatively determined by analysing the top and bottom phases on SDS-PAGE. A Phast System (Amersham Pharmacia Biotech, Uppsala, Sweden) was used and the gels were homogenous 20% SDS-gels. The gels were stained with Coomassie R350 and analysed by scanning with a densitometer (Personal Densitometer SI, Molecular Dynamics, Sunnyvale, Calif., U.S.A.).

The concentration of apolipoprotein A-1 when partitioning E. coli extract was measured by an ELISA assay (Persson et al., J. Chromatog. 711 (1998) 97–109). A biotin antibody conjugate was used and further coupled to an avidin that was alkaline phosphatase linked. The alkaline posphatase was used as marker and the absorption was measured at 405 nm.

The yield was calculated as:

$$\text{Yield}=(C^t_{Apo}*V^t)/C_{Apo}*V)$$

where $C^t_{Apo}$ is the concentration of apolipoprotein A-1 in the top phase and $V^t$ is the volume of the top phase, $C_{Apo}$ is the concentration of apolipoprotein A-1 in the starting material and V is the volume of material added to the system. The purification factor of apolipoprotein A-1 in the systems was calculated as:

$$\text{Purification factor}=(C^t_{Apo}/C^t)/(C_{Apo}/C)$$

where $C^t$ is the protein concentration in the top phase and C is the protein concentration in the starting material.

RESULTS

The water/HM-EOPO polymer system.

Figure 2:
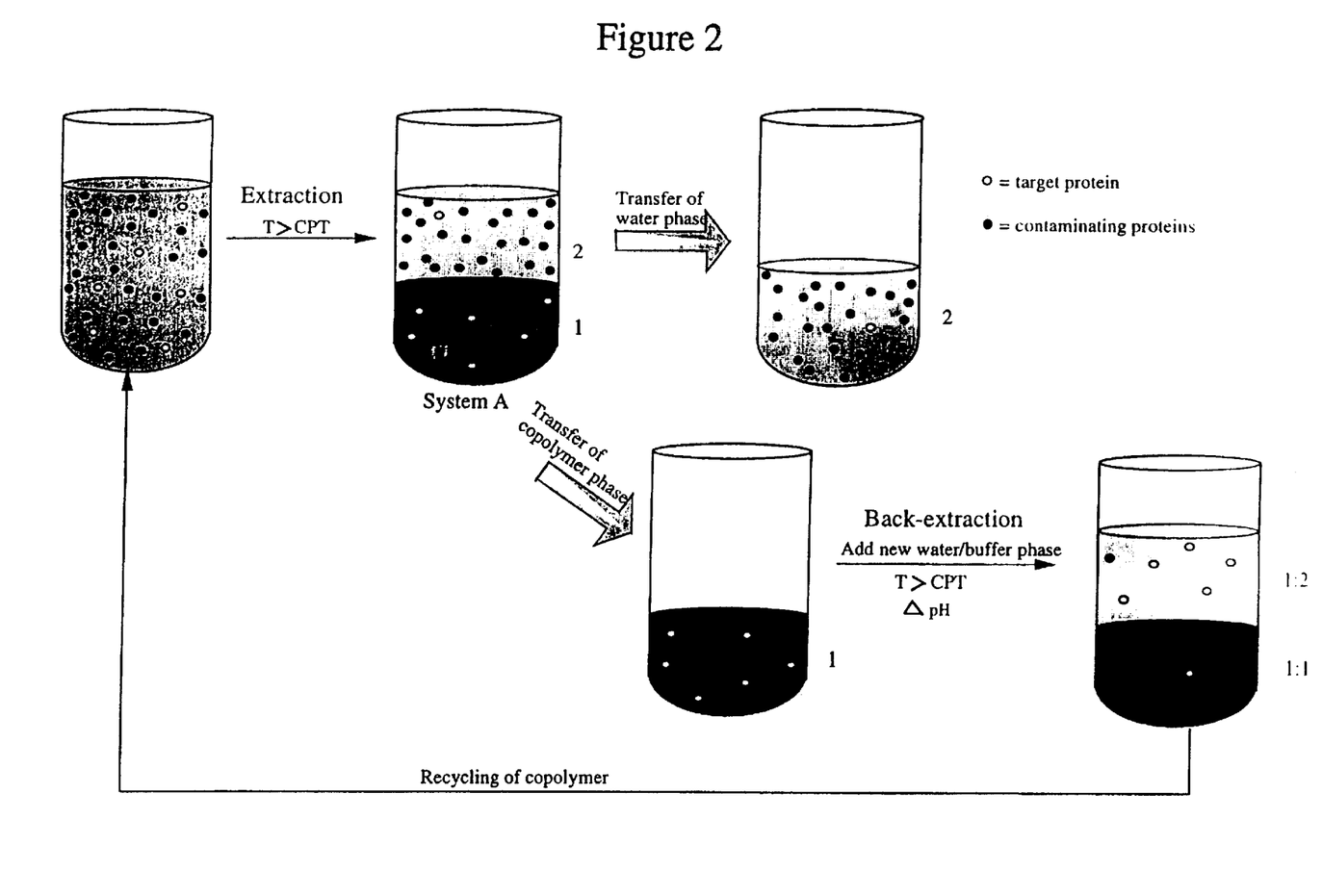
FIG. 2 illustrates steps of separating of contaminating proteins from target proteins in two phase purification of apoliproproterein obtained from *E coli* extract.
Figure 3:
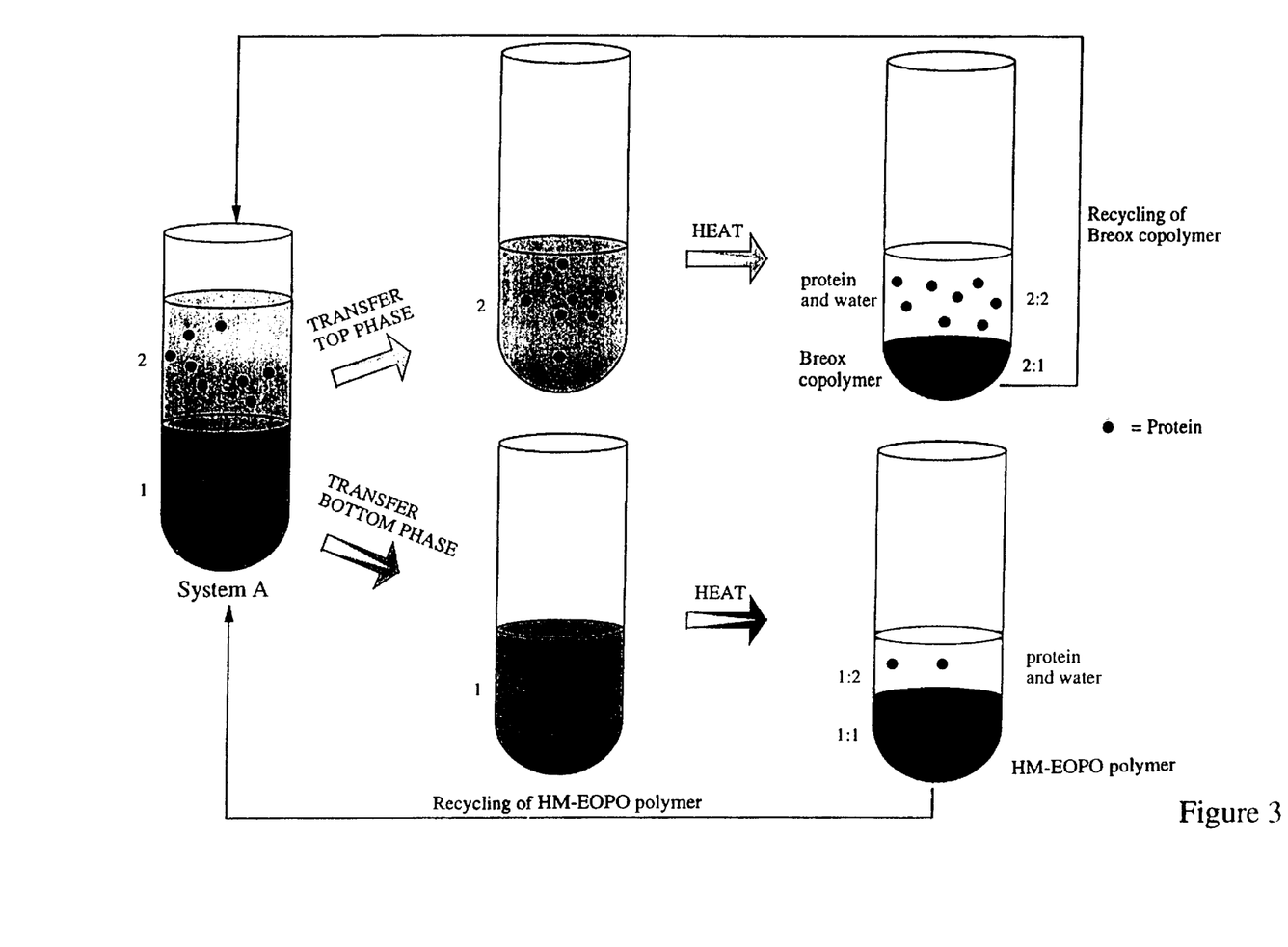
FIG. 3 illustrates steps of concentrating protein in a two phase process utilizing water, HM-EOPO polymer and Breox copolymer.

A temperature versus polymer concentration phase diagrams for the water/HM-EOPO polymer(■)and water/Breox PAG 50A 1000 system (●)are shown in FIG. 1. Phase separation is induced by increasing the temperature. Above the coexistence curve the solution phase separates into two macroscopic phases. The phases formed are both aqueous, one enriched in polymer and one polymer poor (FIG. 1) The lower critical point, which is at the minimum of the coexistence curve, is at 35 HM-EOPO polymer and 14° C. Unlike several studied thermoseparating water/polymer systems (Saeki et al., Polymer 17 (1976) 685-; Karlstrom, J. Phys. Chem. 89 (1985) 4962-; (Johansson et al., Macromolecules 26 (1993) 4478-; and Nystrom et al., Langmuir 11 (1995) 1994–2002) the water/HM=EOPO polymer system shows a strong dependence of phase separation with polymer concentration, i.e, the coexistence curve has a pronounced concave—upward shape. The polymer enriched phase contains a higher concentration of water compared to other thermoseparating random copolymers of EO and PO (Johansson et al., Macromolecules 26 (1993) 4478-; and (Johansson et al., Biochim. Biophys Acta 1290 (1996) 289–298. Between 17 and 30° C. the polymer concentrations in the polymer enriched phase are 5–9% and in the water phase the polymer concentrations are below 1% The water/HM-EOPO polymer systems displays a much greater viscosity than the previously studied thermoseparating water/Ucon on system. The relatively high viscosity of the polymer demanded careful mixing and long equilibration times. In all systems studied the HM-EOPO polymer phase was the lower phase and the water phase the upper phase (FIGS. 2 and 3).

Salt partitioning

In all the studied cases the salts were partitioned stronger to the water phase, K was greater than 1. The partition coefficient of the salts decreased from Na-phosphate (K=1.38) to $Et_3NH$-phosphate (K=1.27) and $NaClO_4$ (K=1.18). The HM-EOPO polymer phase is the more hydrophobic phase and the relative hydrophobicity of the salts increases with lower partition coefficients. This indicates that $NaClO_4$ is the most hydrophobic and Na-phosphate is the most hydrophilic of the salts studied.

Effect of different salts on the partitioning of proteins

For the systems with composition as described in Methods above the cloud points were 14° C. for the $NaClO_4$ containing system, 13° C. for $Et_3NH$-phosphate and 9° C. for sodium phosphate containing system. The $NaClO_4$ and $Et_3NH$-phosphate containing systems were separated at 26° C. The sodium phosphate containing system was separated at 22° C. Each system was separated approximately 13° C. above the cloud point. By doing this the systems were at an equal distance from the critical point and the volume ratio of the phases became very similar. Thus the systems became comparable. In this section all partitioning studies were performed at pH 7.0.

a) The negatively charged apolipoprotein A-1, pI 5.6–5.7 (Brouillette et al., Biochom. Biophys. Acta 1256 (1995) 103–109), was strongly partitioned to the polymer enriched phase with K values below 0.02. The strongest partitioning was obtained with $Et_3NH$-phosphate in the system (K=0.005). The weakest partition to the HM-EOPO polymer phase was obtained with $NaClO_4$ in the system.

b) The negatively charged BSA pI 5.0 (Righetti et al., J. Chromat. 220 (1981) 115–194), was partitioned more to the water phase compared to apolipoprotein A-1. The system containing $NaClO_4$ gave the strongest partitioning to the water phase. There was only a small difference in partition coefficient between the $Et_3NH$-phosphate and the sodium phosphate containing systems.

c) Lysozyme, pI 11.0 (Righetti et al., J. Chromat. 220 (1981) 115–194), partitioned strongest to the polymer enriched phase when $NaClO_4$ was present (K=0.6). The preference for the polymer enriched phase was, however, in this case much weaker than that of apolipoprotein A-1. As in the case for BSA, the salts $Et_3NH$-phosphate and sodium phosphate gave similar partition coefficients and lysozyme was partitioned to the water phase. No significant loss of the enzyme activity was found in these systems. The recovered lysozyme activities in top and bottom phases together were 102, 103 and 103% in $NaClO_4Et_3NH$-phosphate and Na-phosphate systems.

Effect of different phase separation temperatures on the partitioning.

The temperature strongly affects polymer concentrations in the phases (see FIG. 1). The results showed how the partition coefficient of apolipoprotein A-1 changed with temperature. The system composition was 4% (w/w) HM-EOPO polymer, 60 mM sodium phosphate, pH 7.0, and the concentration of apolipoprotein A-1 was 1.0 mg/ml Apolipoprotein A-1 had a preference for the polymer enriched phase at all the studied temperatures. The strongest partitioning to the polymer enriched phase was obtained between 22 and 32° C. with K values at 0.02. Above 40° C. the protein was still partitioned to the polymer enriched phase although much less strongly (K=0.5–0.6 at 50 and 60° C.).

Effect of pH on the partitioning of BSA.

The system composition in these experiments was 4% (w/w) HM-EOPO polymer, 100 mM $NaClO_4$, 10 mM buffer and 1 mg/ml BSA. The used buffers were sodium citrate (pH 3.0), sodium tartrate (pH 5.0) and sodium phosphate (pH 6.0 and 7.0). The pH values measured in the top phase, after separation, were 3.3, 4.3, 5.0, 6.0 and 7.0, respectively. Uncharged (pH 5.0) and negatively charged (pH above 5.0) BSA was partitioned more to the water phase. There was a dramatic decrease of the partition coefficient below the isoelectric point of BSA, K=1.9 at pH 5.0, K=0.03 at pH 9.3 and K=0.01 at pH 3.3. In order to compare the effect at low pH of a different salt, partitioning of BSA in a water/Bermodol system with Na-phosphate (100 mM) as the only salt was carried out. The pH was 4.3 and the K-value in this system was 1.2±0.1. Thus the change of anion from phosphate to $ClO_4^-$ caused an extreme partitioning to the polymer enriched phase.

Back-extraction

The technique of back-extraction from the HM-EOPO polymer phase to the water phase was studied with pure apolipoprotein A-1 (see principles in FIG. 2). This protein was partitioned in a 4% HM-EOPO polymer-water system and separated at 27° C. The salt and buffer concentration in the systems were 20 mm Tris-HCl pH 7.4, 150 mm NaCl, 10 mM EDTA and 0.1% Tween 80. Apolipoprotein A-1 was partitioned strongly to the HM-EOPO polymer phase at 27° C. (K=0.015±0.005). 96± of the apolipoproterin A-1 was detected in this phase. The top water phase was removed and exchanged with an equal volume of 10 mM Tris-HCL buffer pH 8.5 and 100 mM of $NaClO_4$. The system was mixed and allowed to separate again at 50° C. for 20 min. After this treatment 94±1% of the protein that previously was partitioned to the HM-EOPO polymer phase was back-extracted into the new water phase with a partition coefficient K=4.0±0.1. Thus the total recovery of protein was 90±1%.

Purification of apolipoprotein A-1 from human plasma.

Human plasma was used as protein solution for the isolation of apolipoprotein A-1 by partitioning in water/HM-EOPO polymer system Systems with addition of 100 mM $NaClO_4$ were studied and in other systems no extra salt was added. The pH in the systems was 7.8. Albumin is the dominating protein in human plasma, pI 4.8 (18), and human albumin was expected to have a partitioning behaviour quite similar to (BSA) Therefore $NaClO_4$ was added to direct albumin into the water phase. The phase separation was performed at 26° C. for 80 min. The results from the gel electrophoresis show that apolipoprotein A-1 was partitioned almost exclusively to the polymer enriched phase and albumin was partitioned with a preference for the water phase. There was almost no change in partitioning of total protein when comparing the systems with and without addition of $NaClO_4$ K=5.6±0.5 and K=4.7±0.5, respectively. For apolipoprotein A-1 the corresponding partition coefficients were K=0.09±0.01 and K=0.08±0.01, respectively. A purification factor of about 7 was achieved by the extraction of apolipoprotein A-1 to the HM-EOPO polymer phase in the water/HM-EOPO polymer system.

Purification of apolipoproterin A-1 from *E. coli* extract with back-extraction.

The purification of recombinant apolipoprotein A-1 from a cell free fermentation solution of *E. coli* was studied. The *E. coli* extract was partitioned in a 4% water/HM-EOPO polymer system. In the system a buffer containing 20 mM Tris-HCL pH 7.4, 150 mM NaCl, 10 mM EDTA and 0.1% Tween 80 was used. The system was allowed to separate into two phases for 60 min 30° C. in a water bath. In Table 4 the partition coefficient for apolipoprotein A-1 in the first extraction system is shown, K=0.04±0.01. Apolipoprotein A-1 was strongly partitioned to the HM-EOPO polymer phase whereas the majority of contaminating more hydrophilic proteins were partitioned to the water phase. Apolipoprotein A-1 was purified about 7-fold (7±2) by partitioning to the HM-EOPO polymer phase and the recovery of the protein in this phase was more than 95%.

The technique for back-extraction developed for pure apolipoprotein A-1 was used in the purification of apolipoprotein A-1 from *E. coli* extract. Apolipoprotein A-1 was extracted to the HM-EOPO polymer phase and contaminating proteins were removed with the water phase. A new water phase of equal volume containing Tris-HCL pH 8.5 and 100 mm $NaClO_4$ was added (see FIG. 2). After thermoseparation at 50° C. the apolipoprotein A-1 was extracted into the water phase with K=6.0±1. The back-extraction could be performed with a yield of more than 95% and with a purification factor of 7±2. The total recovery of apolipoprotein A-1 was more than 90%.

Two-polymer two-phase system

In separate experiments the two phase system formed by water, HM-EOPO polymer and Breox PAG 50A 1000 (International Speciality Chemicals Ltd, Southhamptoin, U.K.) was studied. Breox PAG 50A 1000 is a random copolymer with equal amount of ethylene oxide and propylene oxide and has a relatively high cloud point (LCST 50° C. at 10% concentration). It is possible to phase separate both copolymers by increasing the temperature over the copolymer cloud point. See FIG. 3. Compared to PEG/dextran systems relatively low concentrations of copolymers are required to form two phases (2% of each copolymer (w/w)). The aqueous two-phase system composed of Breox/HM-EOPO polymer can be used for separation of proteins. Partitioning of (BSA) and lysozyme can be directed by salt addition in similar way as in PEG/dextran systems. The amphiphilic apolipoprotein A-1 interacts with micelles formed by the HM-EOPO polymer and partitions strongly to the HM-EOPO polymer phase. After thermoseparation of the top Breox, and bottom, HM-EOPO polymer, phases it is possible to recover proteins in water solution and to recover and to recycle the copolymers. After thermoseparating 97.5% of HM-EOPO polymer and 73% of Breox copolymer could be recovered. Apolipoprotein A-1 could be extracted to the HM-EOPO polymer phase from a cell free *E. coli* fermentation solution. Systems with recycled copolymers showed similar purification factors and yields during three polymer recyclings.

FIG. 1. Experimentally determined phase diagram for the water/HM-EOPO system (●) and water/Breox PAG 50A 100 (■).

FIG. 2. Protein purification in the water/polymer aqueous two-phase system. Target protein (white dots) is partitioned to the polymer phase (HM-EOPO polymer) at a temperature over the polymer cloud point temperature (CPT, 14° C.). Contaminating proteins (black dots) are partitioned mainly to the water phase. The phases are separated and for the back-extraction a new water phase is added to the polymer phase. The pH and/or salt) is changed and thermoseparating is performed at a higher temperature than in the first extraction. The target protein is back-extracted to the water phase and the polymer is recycled.

FIG. 3. Protein separation and recycling of polymer in aqueous two-phase system with two thermoseparating polymers. First an aqueous two-phase system composed of the polymers Breox PAG 50A 100 and HM-EOPO polymer is mixed. After phase separation the top Breox and bottom HM-EOPO polymer phases are isolated and transferred to a water bath at a temperature above the cloud point of the polymers. This leads to formation of a water phase and a polymer enriched phase. After removal of the water phase the polymers can be removed and reused in a new aqueous two-phase system.

What is claimed is:

1. A method for separating a predetermined compound including:
   i) partitioning said compound in a two-phase system, system A, wherein in said two-phase system, phase 1 is a phase rich in thermoseparating polymer (I) and phase 2 is a phase poor in thermoseparating polymer (I), the improvement comprising:
      said thermoseparating polymer (I) being a micell-forming thermoseparating polymer giving two phases when mixed with water to a concentration of its lowest critical solution temperature and then raised from a temperature below its lowest critical solution temperature to above its lowest critical solution temperature, both of said phases having a water concentration of at least 70%;
   and optionally,
      said phase 2 containing at least one agent that is cloud point-decreasing for thermoseparating polymer (I); and
   ii) collecting said phase 1 or phase 2 containing said compound.

2. The method of claim 1, wherein said thermoseparating polymer (I) has a lowest critical solution temperature that is ≦90° C.

3. The method of claim 1, wherein phase 2 is the phase collected in step (ii) and then phase 2 is subjected to a further phase separation directing the compound to be separated into the phase poor in polymer (II), phase 2:2, and optionally the phase rich in polymer (II), phase 2:1, is recirculated.

4. The method of claim 2, wherein said lowest critical solution temperature is ≦70° C.

5. The method of claim 2, wherein said lowest critical solution temperature is ≦70° C.

6. The method of claim 2, wherein said lowest critical solution temperature is ≦30° C.

7. The method of claim 1, wherein said phase 2 contains at least one of said at least one agent that is cloud-point decreasing is a water-soluble polymer (II) that is incompatible with polymer (I).

8. The method of claim 7, wherein said water-soluble polymer (II) is selected from the group consisting of water-soluble forms of cellulose, dextran, starch, random or block copolymers comprising ethylene oxide and/or propylene oxide without derivatised terminals, and polyethylene glycol.

9. The method of claim 1, wherein said phase 1 and phase 2 are physically separated from each other whereupon thermoseparating polymer (I) in phase 1 or polymer (II) in phase 2, or polymer (I) in phase 1 and polymer (II) in phase 2 are recirculated and used in said system A in a second run of the method.

10. The method of claim 1, wherein said phase 1 is the phase collected in step (ii) and then phase 1 is subjected to a further phase separation directing the compound to be separated into the phase poor in thermoseparating polymer (I), phase 1:2, and optionally the phase rich in polymer, phase 1:1, is recirculated.

11. The method of claim 1, wherein the compound to be separated exhibits a pH-dependent charge and partitions between phase 1 and phase 2 dependent upon its charge, and the pH of the system is selected for maximal partitioning of the compound to be separated to the phase to be collected in step (ii).

12. The method of claim 1, wherein the temperature is selected to achieve a maximal partitioning of the compound to be separated to the phase to be collected in step (ii).

13. The method of claim 1, wherein one or more substances are present in system A, said substances having the ability to improve the partitioning of the compound to be separated to the phase to be collected in step (ii) and said substances are adapted as to type and concentration so that a maximal partitioning of the compound to be separated to the phase to be collected in step (ii) is achieved.

14. The method of claim 13, wherein the compound to be separated is electrically charged and at least one of said one or more substances is a salt containing a counterion improving the partitioning of the compound.

15. The method of claim 13, wherein at least one of said substances is a detergent having affinity for phase 1.

16. The method of claim 1, wherein the compound to be separated exhibits a peptide structure.

17. The method of claim 16, wherein said peptide structure is a oligo- or polypeptide structure.

18. The method of claim 16, wherein said peptide structure is a protein.

19. The method of claim 1, wherein the micell-forming thermoseparating polymer (I) exhibits a central polymeric part of hydrophilic monomeric units that are identical or different and each terminal end is a hydrophobic group.

20. The method of claim 19, wherein in each hydrophilic monomeric unit the ratio between the number of oxygen atoms and the number of carbon atoms is at least 1/4, and wherein in the hydrophobic groups the ratio between number of oxygen atoms and number of carbon atoms is at most 1/5.

21. The method of claim 20, wherein said ratio between the number of oxygen atoms and the number of carbon atoms is at least 1/3.

22. The method of claim 1, wherein said phase 2 contains at least one agent that is cloud point-decreasing is a polymer (II) incompatible with polymer (I) or is a salt.

* * * * *